United States Patent [19]

Fried et al.

[11] 3,958,012
[45] May 18, 1976

[54] D 2-(6-SUBSTITUTED-2-NAPHTHYL)-PROPANALS

[75] Inventors: John H. Fried; Ian T. Harrison, both of Palo Alto, Calif.

[73] Assignee: Syntex Corporation, Palo Alto, Calif.

[22] Filed: Mar. 27, 1975

[21] Appl. No.: 562,714

Related U.S. Application Data

[60] Division of Ser. No. 301,595, Oct. 27, 1972, Pat. No. 3,891,712, which is a continuation of Ser. No. 865,216, Oct. 9, 1969, which is a continuation-in-part of Ser. Nos. 741,900, July 21, 1968, Pat. No. 3,626,012, and Ser. No. 814,855, April 9, 1969, Pat. No. 3,663,713.

[52] U.S. Cl. .............................................. 424/333
[51] Int. Cl.$^2$ ........................................ A61K 31/11
[58] Field of Search ....................................... 424/333

*Primary Examiner*—Stanley J. Friedman
*Attorney, Agent, or Firm*—Joseph I. Hirsch; William B. Walker

[57] ABSTRACT

The d 2-(6-substituted-2-naphthyl)propanals of this invention are prepared by oxidizing the corresponding 2-(6-substituted-2-naphthyl)-1-propanols or by reducing d 2-(6-substituted-2-naphthyl)propionic acids, the 6-substituent being a methyl, ethyl, isopropyl, cyclopropyl, trifluoromethyl, vinyl, ethynyl, fluoro, chloro, methoxy, methoxymethyloxy, difluoromethoxy, methylthio, methoxymethylthio or difluoromethylthio group. The products have anti-inflammatory, analgesic and antipyretic activities.

9 Claims, No Drawings

D 2-(6-SUBSTITUTED-2-NAPHTHYL)-PROPANALS

This application is a divisional application of application Ser. No. 301,595, filed Oct. 27, 1972, now U.S. Pat. No. 3,891,712, which is a continuation of application Ser. No. 865,216, filed Oct. 9, 1969 which is, in turn, a continuation-in-part of U.S. patent applications Ser. No. 741,900 filed July 2, 1968, now U.S. Pat. No. 3,626,102, and Ser. No. 814,855 filed Apr. 9, 1969, now U.S. Pat. No. 3,663,713.

This invention relates to d 2-(6-substituted-2-naphthyl)-propanals.

The d 2-(6-substituted-2-naphthyl)propanals of this invention can be represented by the following general formula:

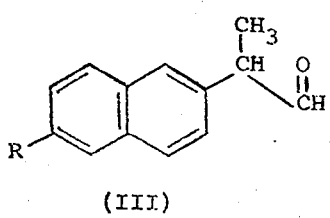

(III)

In the above formula, R is a methyl, ethyl, isopropyl, cyclopropyl, trifluoromethyl, vinyl, ethynyl, fluoro, chloro, methoxy, methoxymethyloxy, difluoromethoxy, methylthio, methoxymethylthio or difluoromethylthio group.

The compounds of Formula III exhibit anti-inflammatory, analgesic, and anti-pyretic activities; accordingly, these compounds are employed in the treatment and alleviation of inflammation, pain and pyrexia in mammals.

The compounds of Formula III are especially useful in the treatment of inflammation, such as inflammatory conditions of the muscular skeletal system, skeletal joints and other tissues. Accordingly, these compounds are useful in the treatment of conditions characterized by inflammation, such as rheumatism, contusion, lacerations, arthritis, bone fractures, post-traumatic conditions and gout. In those cases in which the above conditions include pain and pyrexia coupled with inflammation, the instant compounds are useful for the relief of these conditions as well as the inflammation.

A measure of anti-inflammatory activity according to the Carrageenin induced endema in Winter et al. The *Proceedings of The Society for Experimental Biology and Medicine*, Vol. III, 544 (1962) shows d 2-(6-methoxy-2-naphthyl)propanal to have 8 times the activity of phenyl butazone.

The preferred manner of administration is oral administration which provides the use of the convenient daily dosage regimen which can be adjusted accordingly to the degree of affliction. Generally, a daily dose of from 0.1 mg. to 60 mg. of the active compound per kilogram of body weight of the mammal is employed. Most conditions respond to the treatment comprising a dosage level in the order of 0.5 to 5 mg. For such oral administration a pharmaceutically acceptable nontoxic composition can be formed by the incorporation of any of the normally employed excipients. Suitable pharmaceutical excipients include starch, glucose, lactose, sucrose, gelatin, malt, rice, flour, chalk, silica gel, magnesium stearate, sodium stearate, glyceryl monostearate, talc, sodium chloride, dried skim milk, glycerol, propylene glycol, water, ethanol and the like. These compositions take the forms of solutions, suspensions, tablets, pills, capsules, powders, sustained release formulations, and the like. In addition, these compounds can be administered in conjunction with other medicinal agents depending upon the specific condition being treated.

The compounds of Formula III are prepared by a procedure which can be represented as follows:

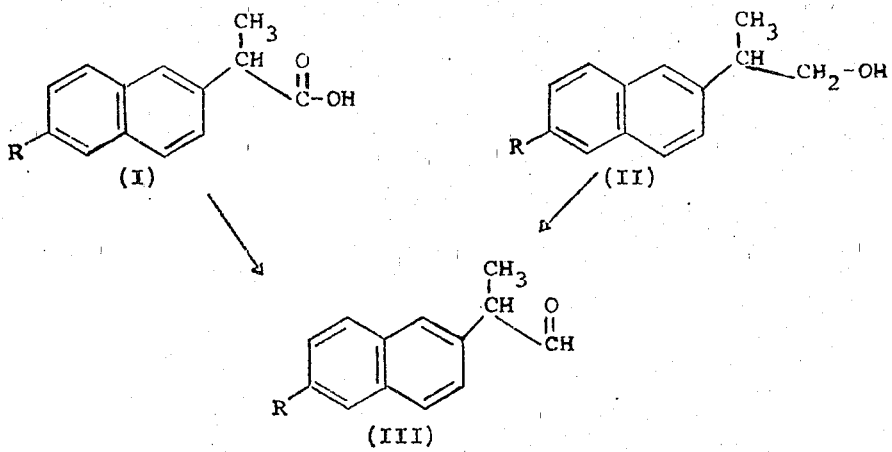

In the above formulas, R is as previously defined.

The compounds of Formula III can be prepared from the corresponding d 2-(6-substituted-2-naphthyl)propionic acids represented by Formula I by the following procedure. The latter compounds are first converted to the corresponding acid chlorides by reaction with thionyl chloride in benzene under reflux followed by evaporation of the solvent. The residual acid chloride is then treated with 2 equivalents of lithium aluminum tritertiarybutoxyhydride in an ether solvent such as tetrahydrofuran, tetrahydropyran, dimethoxyethane and the like at a temperature of from −80° to 0°C for from 30 minutes to 12 hours to yield the compounds of Formula III which can be recovered by conventional procedures. For example, the reaction mixture can be mixed with water, extracted with benzene. The benzene phase can then be evaporated in vacuo to dryness, and the residue recrystallized from dichloromethane-hexane.

The preferred process for preparing the compounds of Formula III comprises oxidizing the optical isomer propanols of Formula II corresponding to the respective d 2-(6-substituted-2-naphthyl)propionic acids with chromium trioxide-pyridine complex, the molar ratio of the complex to the compounds of Formula II being within the range of from 0.8:1 to 10:1, preferably about 5:1. The reaction is conducted in an inert organic solvent such as a halogenated hydrocarbon, e.g. dichloromethane, chloroform, carbon tetrachloride, etc.; hydrocarbons such as hexane, heptane, benzene, toluene, and the like; amines such as dimethylaniline, pyridine, collidine, quinoline, lutidine, etc.; and ethers such as tetrahydrofuran, tetrahydropyran, dimethoxyethane, diethylether and the like. The reaction is carried out at a temperature of from 0° to 60°C, the time required being dependent upon the reaction temperature. Times of from 1 to 48 hours are usually sufficient. The compounds of Formula II are then isolated from the reaction mixture by conventional procedures. For example, the reaction mixture can be chromatographed on silica gel, eluting with dichloromethane to yield the compounds of Formula II which can be crystallized from dichloromethanehexane.

Compounds of Formula I can be prepared by any of several methods. One such method by which they can be prepared is described in U.S. patent applications Ser. No. 608,997, filed Jan. 13, 1967 and Ser. No. 694,771, filed Dec. 7, 1967, both now abandoned. This method involves the reaction of a β-substituted naphthalene with acetyl chloride in nitrobenzene in the presence of at least 3 molar equivalents of aluminum chloride to afford the corresponding 6-substituted-2-acetyl-naphthalene derivative. The resulting derivative is heated with morpholine in the presence of sulfur at about 150°C; the resulting product is refluxed with concentrated hydrochloric acid to furnish the corresponding 2-(6-substituted-2-naphthyl)acetic acid derivative. The addition of a methyl group at the C-2 position is carried out by esterifying the 2-(6-substituted-2-naphthyl)acetic acid derivative by conventional methods such as by treatment with a diazoalkane, such as diazomethane, in ether or with an alkanol such as methanol, in the presence of boron trifluoride to afford the corresponding alkyl ester. The ester product is then treated with sodium hydride in an ether solvent, such as 1,2-dimethoxyethane; and then treated with a methyl halide, such as methyl iodide, to afford the corresponding 2-(6-substituted-2-naphthyl)propionic acid alkyl ester, which is hydrolyzed to yield the unresolved compounds of Formula I.

The d-isomers of Formula I can be obtained by selective biological degradation or by the preparation of diastereo isomer salts of the 2-(6-substituted-2-naphthyl)propionic acid derivatives with resolved optically active amine bases such a cinchonidine and then separating the thus formed diastereo isomers by fractional crystallization. The separated diastereo isomer salts are then acid cleaved to yield the respective d 2-(6-substituted-2-naphthyl)propionic acid derivatives.

The compounds of Formula II together with methods for their preparation have been described in U.S. patent application Ser. No. 741,904 filed July 2, 1968 now U.S. Pat. No. 3,641,161. For example, they can be prepared by reducing the compounds of Formula I with lithium aluminum hydride in an inert organic ether solvent. The compounds of Formula I are treated with at least 0.75 molar equivalents of lithium aluminum hydride, preferably from 1 to 2.5 molar equivalents. Suitable inert organic ethers include diethyl ether, dipropyl ether, diisopropyl ether, dibutyl ether, tetrahydrofuran, tetrahydropyran, dimethoxyethane and the like. The reaction is carried out at a temperature between 0°C and the boiling point of the solvent employed, preferably between 15°C and 45°C.

The compounds of Formula II are then isolated by destroying the excess lithium aluminum hydride, if any, such as by adding excess ethyl acetate. The mixture is then diluted with water, filtered and extracted with an inert organic solvent immiscible with water. The organic phase can be evaporated to dryness, and the compounds of Formula II obtained by recrystallization from acetone-hexane. Alternatively, the compounds of Formula I can be reduced by treating them with diborane in tetrahydrofuran at a temperature between 0° and 65°C.

PREPARATION 1

To a mixture of 1.6 g. of 2-methoxynaphthalene, 1.6 g. of acetyl chloride, and 20 ml. of nitrobenzene, there are added 4.0 g. of aluminum chloride. The resulting mixture is stirred for 48 hours at 25°C; then it is washed with water until free of chloride ion. The mixture is dried over sodium sulfate and evaporated under reduced pressure. The residue, 2-acetyl-6-methoxynaphthalene, is refluxed in 2 ml. of morpholine containing one-half gram of sulfur for 2 hours; the reaction mixture is then filtered and evaporated. The resulting reaction derivative is extracted with diethyl ether; the extracts are combined and evaporated. The residue is refluxed in 10 ml. of concentrated hydrochloric acid for 2 hours, cooled to 25°C, and neutralized with aqueous sodium hydroxide. The mixture is then extracted with ether and the extracts are combined, washed with water to neutrality, dried and evaporated to yield 2-(6-methoxy-2-naphthyl)acetic acid.

Similarly,
2-(6-methyl-2-naphthyl)acetic acid,
2-(6-ethyl-2-naphthyl)acetic acid,
2-(6-isopropyl-2-naphthyl)acetic acid,
2-(6-cyclopropyl-2-naphthyl)acetic acid,
2-(6-trifluoromethyl-2-naphthyl)acetic acid,
2-(6-vinyl-2-naphthyl)acetic acid,
2-(6-ethynyl-2-naphthyl)acetic acid,
2-(6-fluoro-2-naphthyl)acetic acid,
2-(6-chloro-2-naphthyl)acetic acid,
2-(6-methoxy-2-naphthyl)acetic acid,
2-(6-methoxymethyloxy-2-naphthyl)acetic acid,
2-(6-difluoromethoxy-2-naphthyl)acetic acid,
2-(6-methylthio-2-naphthyl)acetic acid,
2-(6-methoxymethylthio-2-naphthyl)acetic acid, and
2-(6-difluoremethylthio-2-naphthyl)acetic acid
are prepared from the corresponding β-substituted naphthalene by this procedure.

PREPARATION 2

To a mixture of 22 g. of methyl 2-(6-methoxy-2-naphthyl)acetate (prepared by treating 20.5 g. of 2-(6-methoxy-2-naphthyl)acetic acid with 4.5 g. of diazomethane in ether), and 2.5 g. of sodium hydride in 150 ml. of 1,2-dimethoxyethane; 25 g. of methyl iodide are added. The reaction mixture is allowed to stand for several hours; then it is diluted with ethanol followed by water and extracted with methylene chloride. The extracts are combined, washed with water to neutrality, dried over sodium sulfate, filtered and evaporated to yield methyl 2-(6-methoxy-2-naphthyl)propionate.

The resulting product is added to a mixture of 15 g. of sodium carbonate, 200 ml. of methanol and 25 ml. of water. The reaction mixture is allowed to stand for 24 hours; then the mixture is acidified with 200 ml. of two normal hydrochloric acid. The acidified mixture is extracted with methylene chloride; the extracts are combined, washed with water, dried over sodium sulfate and evaporated to yield 2-(6-methoxy-2-naphthyl)propionic acid.

Similarly, the following 2-(6-substituted-2-naphthyl)propionic acid derivatives are prepared from the corresponding 2-(6-substituted-2-naphthyl)acetic acid derivatives:

2-(6-methyl-2-naphthyl)propionic acid,
2-(6-ethyl-2-naphthyl)propionic acid,
2-(6-isopropyl-2-naphthyl)propionic acid,
2-(6-cyclopropyl-2-naphthyl)propionic acid,
2-(6-trifluoromethyl-2-naphthyl)propionic acid,
2-(6-vinyl-2-naphthyl)propionic acid,
2-(6-ethynyl-2-naphthyl)propionic acid,
2-(6-fluoro-2-naphthyl)propionic acid,
2-(6-chloro-2-naphthyl)propionic acid,
2-(6-methoxy-2-naphthyl)propionic acid,
2-(6-methoxymethyloxy-2-naphthyl)propionic acid,
2-(6-difluoromethoxy-2-naphthyl)propionic acid,
2-(6-methylthio-2-naphthyl)propionic acid,
2-(6-methoxymethylthio-2-naphthyl)propionic acid, and
2-(6-difluoromethylthio-2-naphthyl)propionic acid.

PREPARATION 3

A 230 g. portion of dl 2-(6-methoxy-2-naphthyl)propionic acid in methanol is dissolved in 4.6 l. of warm methanol. The resulting solution is boiled until it becomes turbid; then sufficient methanol is added to make the solution clear again. This hot solution is added to a solution of 296 g. of cinchonidine in 7.4 l. of methanol heated to about 60°C. The solutions are combined while stirring, and the combined mixture is then allowed to reach room temperature over a 2 hour period. After the reaction mixture has reached room temperature, it is stirred for an additional 2 hours and then filtered. The filtered solids are washed with several portions of cold methanol and dried.

100 Grams of the cinchonidine salt crystals are added to a stirred mixture of 600 ml. of ethyl acetate and 450 ml. of a 2 N aqueous hydrochloric acid. After the mixture has been stirred for 2 hours, the ethyl acetate layer is removed and washed with water to neutrality, dried over sodium sulfate and evaporated to yield d 2 -(6-methoxy-2-naphthyl)propionic acid.

PREPARATION 4

To a mixture of 0.4 g. of lithium aluminum hydride and 100 ml. of ethyl ether, there is added a mixture of 2.3 g. of d 2-(6-methoxy-2-naphthyl)propionic acid and 100 ml. of ethyl ether. The mixture is stirred at 0°C for 30 minutes, and 10 ml. of ethyl acetate is added. After 1 hour, 4 ml. of water is added to the mixture. The resulting mixture is filtered and evaporated under reduced pressure to yield l 2-(6-methoxy-2-naphthyl)-1-propanol.

Repeating the above procedure with the d isomers of the compounds of Preparation 2 yields the corresponding optical isomers of 2-(6-substituted-2-naphthyl)-1-propanols.

This invention is further illustrated by the following specific but non-limiting examples.

EXAMPLE 1

A solution of 23 g. of d 2-(6-methoxy-2-naphthyl)propionic acid in 100 ml. of benzene and 20 ml. of thionyl chloride is heated under reflux for 2 hours. The reaction mixture is then evaporated in vacuo to yield the corresponding acid chloride. A solution of the residue in 300 ml. of tetrahydrofuran is cooled to −80°C and treated with 47 g. of lithium aluminum tritertiarybutoxyhydride (2 molar equivalents). After stirring the reaction mixture at this temperature for 1 hour, the mixture is allowed to warm up to room temperature and is poured into water. The mixture is then extracted with benzene, and the organic phase is evaporated in vacuo to yield d 2-(6-methoxy-2-naphthyl)propanal which is recrystallized from dichloromethane-hexane.

Repeating this procedure with the other d isomers of the compounds of Preparation 2 yields the corresponding d 2-(6-substituted-2-naphthyl)propanal derivatives, e.g. d 2-(6-methyl-2-naphthyl)propanal, d 2-(6-ethyl-2-naphthyl)propanal, d 2-(6-isopropyl-2-naphthyl)propanal, d 2-(6-cyclopropyl-2-naphthyl)propanal, d 2-(6-fluoro-2-naphthyl)propanal, d 2-(6-chloro-2-naphthyl)propanal, d 2-(6-trifluoromethyl-2-naphthyl)propanal, d 2-(6-methylthio-2-naphthyl)propanal, d 2-(6-vinyl-2-naphthyl)propanal, d 2-(6-difluoromethoxy-2-naphthyl)propanal and d 2-(6-difluoromethylthio-2-naphthyl)propanal.

EXAMPLE 2

A solution of 580 mg. of l 2-(6-methoxy-2-naphthyl)-1-propanol in 25 ml. of dichloromethane is treated with 2.9 g. of chromium trioxide-pyridine complex and stirred at room temperature for 5 hours. The mixture is then poured onto a column of silica gel. Elution with dichloromethane yields 260 mg. of d 2-(6-methoxy-2-naphthyl)propanal which is recrystallized from dichloromethane-hexane. (m.p. 70°–72°C, $[\alpha]_D + 151°$ in dioxane).

Repeating the above procedure with the other products of Preparation 4 yields the corresponding d 2-(6-substituted-2-naphthyl)propanals, e.g. d 2-(6-methyl-2-naphthyl)propanal, d 2-(6-ethyl-2-naphthyl)propanal, d 2-(6-isopropyl-2-naphthyl)propanal, d 2-(6-cyclopropyl-2-naphthyl)propanal, d 2-(6-fluoro-2-naphthyl)propanal, d 2-(6-chloro-2-naphthyl)propanal, d 2-(6-trifluoromethyl-2-naphthyl)propanal, d 2-(6-methylthio-2-naphthyl)propanal, d 2-(6-vinyl-2-naphthyl)propanal, d 2-(6-difluoromethoxy-2-naphthyl)propanal, and d 2-(6-difluoromethylthio-2-naphthyl)propanal.

EXAMPLE 3

| Ingredients | Quantity per tablet, mgs. |
|---|---|
| d 2-(6-methoxy-2-naphthyl)propanal | 10 |
| cornstarch | 200 |
| sucrose | 40 |

The above ingredients are thoroughly mixed and pressed into single scored tablets.

EXAMPLE 4

| Ingredients | Quantity per tablet, mgs. |
| --- | --- |
| d 2-(6-methoxy-2-naphthyl)propanal | 25 |
| cornstarch | 100 |
| lactose | 393 |
| magnesium stearate | 2 |

The above ingredients are mixed intimately and pressed into single scored tablets.

EXAMPLE 5

| Ingredient | Quantity per capsule, mgs. |
| --- | --- |
| d 2-(6-methyl-2-naphthyl)propanal | 50 |
| lactose | 190 |

The above ingredients are mixed and introduced into a hard-shell gelatin capsule.

We claim:

1. A pharmaceutical composition for use in treatment of inflammation, pain and fever in mammals which comprises an amount therapeutically effective to treat inflammation, pain, or pyrexia of a compound represented by the formula:

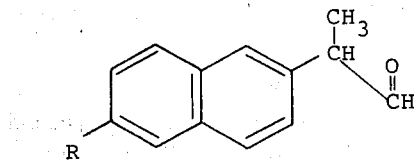

where R is methyl, ethyl, isopropyl, cyclopropyl, trifluoromethyl, vinyl, ethynyl, fluoro, chloro, methoxy, methoxymethyloxy, difluoromethoxy, methylthio, methoxymethylthio or difluoromethylthio, in combination with a non-toxic, pharmaceutically acceptable excipient.

2. The composition of claim 1 wherein said compound is d 2-(6-methoxy-2-naphthyl)propanal.

3. The composition of claim 1 wherein said compound is d 2-(6-methylthio2-naphthyl)propanal.

4. The composition of claim 1 wherein said compound is d 2-(6-methyl-2-naphthyl)propanal.

5. The composition of claim 1 wherein said compound is d 2-(6-difluoromethoxy-2-naphthyl)propanal.

6. The composition of claim 1 wherein said compound is d 2-(6-chloro-2-naphthyl)propanal.

7. The composition of claim 1 wherein said composition contains from 0.1 mg. to 60 mg. of said compound per kilogram of body weight of said mammal.

8. A pharmaceutical composition for use in treatment of inflammation, pain and fever which comprises, in a dosage form suitable for oral administration, 0.1 mg. to 60 mg. per kilogram of body weight of a compound represented by the formula:

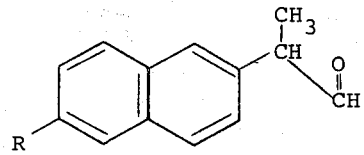

where R is methyl, ethyl, isopropyl, cyclopropyl, trifluoromethyl, vinyl, ethynyl, fluoro, chloro, methoxy, methoxymethyloxy, difluoromethoxy, methylthio, methoxymethylthio or difluoromethylthio, in combination with a non-toxic, pharmaceutically acceptable excipient.

9. The composition of claim 8 wherein said compound is d 2-(6-methoxy-2-naphthyl)propanal.

* * * * *